United States Patent
Ambrosius et al.

(10) Patent No.: US 6,455,279 B1
(45) Date of Patent: Sep. 24, 2002

(54) PROCESS FOR THE PRODUCTION OF NATURALLY FOLDED AND SECRETED PROTEINS BY CO-SECRETION OF MOLECULAR CHAPERONES

(75) Inventors: Dorothee Ambrosius, Munich; Rainer Rudolph, Halle; Joerg Schaeffner, Halle; Elisabeth Schwarz, Halle, all of (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/618,869

(22) Filed: Jul. 19, 2000

(30) Foreign Application Priority Data

Jul. 29, 1999 (EP) .............................................. 99114811

(51) Int. Cl.⁷ ............................. C12P 21/06; C12Q 1/68
(52) U.S. Cl. .......................................... 435/69.1; 435/6
(58) Field of Search ........................ 435/6, 69.1, 71.1; 530/402

(56) References Cited

U.S. PATENT DOCUMENTS

| | | | |
|---|---|---|---|
| 4,757,013 A | | 7/1988 | Inouye et al. |
| 4,933,434 A | | 6/1990 | Rudolph et al. |
| 5,077,392 A | * | 12/1991 | Rudolph et al. ............ 530/402 |
| 5,453,363 A | | 9/1995 | Rudolph et al. |
| 5,593,865 A | | 1/1997 | Rudolph et al. |
| 5,824,502 A | * | 10/1998 | Honjo et al. ................ 435/69.1 |
| 6,083,715 A | * | 7/2000 | Georgiou et al. .......... 435/69.1 |

FOREIGN PATENT DOCUMENTS

| | | |
|---|---|---|
| EP | 0219874 | 4/1987 |
| EP | 510658 | 10/1992 |
| EP | 0774512 | 5/1997 |
| EP | 0885967 | 12/1998 |
| EP | 1054063 | 11/2000 |
| WO | WO 89/06283 | 7/1989 |
| WO | WO 96/14422 | 5/1996 |
| WO | WO 98/18946 | 5/1998 |

OTHER PUBLICATIONS

Zavialov, et al. Biochimica et Biophysica Acta. NL Amsterdam vol. 1388, No. 1 (Oct. 14, 1998) pp. 123–132.

Yokoyama, et al. Bioscience Biotechnol. Biochemistry vol. 62(6) pp. 1205–1210, 1998.

Ehrnsperger, et al. J. Biol. Chem. vol. 274, No. 21 pp. 14867–14874, 1999.

Ehrnsperger, et al. EMBO Journal vol. 16, No. 2 pp. 221–229, 1997.

Abstract corresponding to EP0510658.

Anderson, L. et al., Molecular Microbiology, 26, pp. 121–132 (1997).

Pérez–Pérez, Julián et al., Gene, 158, pp. 141–142 (1995).

Pérez–Pérez, Julián et al., Biochemical and Biophysical Research Communications, 102, pp. 524–529 (1995).

Hayhurst, A., et al. Protein Expression and Purification, vol. 15, pp. 336–343 (1999).

Qiu, J. et al., Applied and Environmental Microbiology, Dec. 1998, vol. 64, No. 12, pp. 4891–4896.

Schmidt, A.M., et al., Protein Engineering vol. 11, No. 7, pp. 601–607 (1998).

Joly J.C., et al., Proc. Natl. Acad. Sci. USA, vol. 95, pp. 2773–2777, Mar. 1998.

Ostermeier, M. et al., J. Biol. Chem. vol. 271, pp. 10616–10622 (1996).

Bothmann, H., et al., Nature Biotechnology vol. 16, Apr. 1998, pp. 376–380.

\* cited by examiner

*Primary Examiner*—Eggerton A. Campbell
*Assistant Examiner*—Shabha Chunduru
(74) *Attorney, Agent, or Firm*—George W. Johnston; Robert A. Silverman

(57) ABSTRACT

A process for the production of a naturally folded eukaryotic polypeptide containing two or several cysteines linked by disulfide bridges by a) culturing prokaryotic cells in which the said prokaryotic cells contain an expression vector which codes for the said polypeptide which contains a prokaryotic signal sequence at the N-terminus, b) secreting the polypeptide into the periplasm or the medium, c) cleaving the signal sequence and isolating the polypeptide from the periplasm or the medium, which is characterized in that a nucleic acid coding for a molecular chaperone is additionally expressed in the said prokaryotic cell and the chaperone is secreted into the periplasm, is suitable for the recombinant production of polypeptides in prokaryotes in a high yield.

16 Claims, 6 Drawing Sheets

SEQUENCE LISTING

<160> NUMBER OF SEQ ID NOS: 10

<210> SEQ ID NO 1
<211> LENGTH: 1881
<212> TYPE: DNA
<213> ORGANISM: Escherichia coli
<220> FEATURE:
<221> NAME/KEY: CDS
<222> LOCATION: (392)..(1591)

<400> SEQUENCE: 1

```
taggcgtatc acgaggccct ttggataacc agaagcaata aaaaatcaaa tcggatttca      60
ctatataatc tcactttatc taagatgaat ccgatggaag catcctgttt tctctcaatt     120
tttttatcta aacccagcg ttcgatgctt ctttgagcga acgatcaaaa ataagtgcct      180
tcccatcaaa aaatattct caacataaaa actttgtgt aatacttgta acgctacatg      240
gagattaact caatctagct agagaggctt tacactttat gcttccggct cgtataatgt      300
gtggaattgt gagcggataa caatttcaca caggaaacag ctatgaccat gattacggat      360
tcactggaac tctagataac gagggcaaaa a atg aaa aag aca gct atc gcg       412
                                 Met Lys Lys Thr Ala Ile Ala
                                  1               5 att gca gtg gca ctg gct ggt ttc gct acc gta gcg cag gcc gga att       460
Ile Ala Val Ala Leu Ala Gly Phe Ala Thr Val Ala Gln Ala Gly Ile
         10                  15                  20 cca gct aag caa gat tat tac gag att tta ggc gtt tcc aaa aca gcg       508
Pro Ala Lys Gln Asp Tyr Tyr Glu Ile Leu Gly Val Ser Lys Thr Ala
     25                  30                  35 gaa gag cgt gaa atc aga aag gcc tac aaa cgc ctg gcc atg aaa tac       556
Glu Glu Arg Glu Ile Arg Lys Ala Tyr Lys Arg Leu Ala Met Lys Tyr
 40                  45                  50                  55 cac ccg gac cgt aac cag ggt gac aaa gag gcc gag gcg aaa ttt aaa       604
His Pro Asp Arg Asn Gln Gly Asp Lys Glu Ala Glu Ala Lys Phe Lys
                 60                  65                  70 gag atc aag gaa gct tat gaa gtt ctg acc gac tcg caa aaa cgt gcg       652
Glu Ile Lys Glu Ala Tyr Glu Val Leu Thr Asp Ser Gln Lys Arg Ala
             75                  80                  85 gca tac gat cag tat ggt cat gct gcg ttt gag caa ggt ggc atg ggc       700
Ala Tyr Asp Gln Tyr Gly His Ala Ala Phe Glu Gln Gly Gly Met Gly
         90                  95                 100 ggc ggc ggt ttt ggc ggc ggc gca gac ttc agc gat att ttt ggt gac       748
Gly Gly Gly Phe Gly Gly Gly Ala Asp Phe Ser Asp Ile Phe Gly Asp
    105                 110                 115 gtt ttc ggc gat att ttt ggc ggc gga cgt ggt cgt caa cgt gcg gcg       796
Val Phe Gly Asp Ile Phe Gly Gly Gly Arg Gly Arg Gln Arg Ala Ala
120                 125                 130                 135 cgc ggt gct gat tta cgc tat aac atg gag ctc acc ctc gaa gaa gct       844
Arg Gly Ala Asp Leu Arg Tyr Asn Met Glu Leu Thr Leu Glu Glu Ala
                140                 145                 150 gta cgt ggc gtg acc aaa gag atc cgc att ccg act ctg gaa gag tgt       892
Val Arg Gly Val Thr Lys Glu Ile Arg Ile Pro Thr Leu Glu Glu Cys
            155                 160                 165 gac gtt tgc cac ggt agc ggt gca aaa cca ggt aca cag ccg cag act       940
Asp Val Cys His Gly Ser Gly Ala Lys Pro Gly Thr Gln Pro Gln Thr
        170                 175                 180 tgt ccg acc tgt cat ggt tct ggt cag gtg cag atg cgc cag gga ttc       988
Cys Pro Thr Cys His Gly Ser Gly Gln Val Gln Met Arg Gln Gly Phe
    185                 190                 195
```

-continued

| | | |
|---|---|---|
| ttc gct gta cag cag acc tgt cca cac tgt cag ggc cgc ggt acg ctg<br>Phe Ala Val Gln Gln Thr Cys Pro His Cys Gln Gly Arg Gly Thr Leu<br>200                           205                  210                   215 | | 1036 |
| atc aaa gat ccg tgc aac aaa tgt cat ggt cat ggt cgt gtt gag cgc<br>Ile Lys Asp Pro Cys Asn Lys Cys His Gly His Gly Arg Val Glu Arg<br>                    220                  225                   230 | | 1084 |
| agc aaa acg ctg tcc gtt aaa atc ccg gca ggg gtg gac act gga gac<br>Ser Lys Thr Leu Ser Val Lys Ile Pro Ala Gly Val Asp Thr Gly Asp<br>                235                  240                   245 | | 1132 |
| cgc atc cgt ctt gcg ggc gaa ggt gaa gcg ggc gag cat ggc gca ccg<br>Arg Ile Arg Leu Ala Gly Glu Gly Glu Ala Gly Glu His Gly Ala Pro<br>250                           255                  260 | | 1180 |
| gca ggc gat ctg tac gtt cag gtt cag gtt aaa cag cac ccg att ttc<br>Ala Gly Asp Leu Tyr Val Gln Val Gln Val Lys Gln His Pro Ile Phe<br>     265                  270                  275 | | 1228 |
| gag cgt gaa ggc aac aac ctg tat tgc gaa gtc ccg atc aac ttc gct<br>Glu Arg Glu Gly Asn Asn Leu Tyr Cys Glu Val Pro Ile Asn Phe Ala<br>280                         285                  290                   295 | | 1276 |
| atg gcg gcg ctg ggt ggc gaa atc gaa gta ccg acc ctt gat ggt cgc<br>Met Ala Ala Leu Gly Gly Glu Ile Glu Val Pro Thr Leu Asp Gly Arg<br>                    300                  305                   310 | | 1324 |
| gtc aaa ctg aaa gtg cct ggc gaa acc cag acc ggt aag cta ttc cgt<br>Val Lys Leu Lys Val Pro Gly Glu Thr Gln Thr Gly Lys Leu Phe Arg<br>             315                  320                  325 | | 1372 |
| atg cgc ggt aaa ggc gtc aag tct gtc cgc ggt ggc gca cag ggt gat<br>Met Arg Gly Lys Gly Val Lys Ser Val Arg Gly Gly Ala Gln Gly Asp<br>330                         335                  340 | | 1420 |
| ttg ctg tgc cgc gtt gtc gtc gaa aca ccg gta ggc ctg aac gaa agg<br>Leu Leu Cys Arg Val Val Val Glu Thr Pro Val Gly Leu Asn Glu Arg<br>     345                  350                  355 | | 1468 |
| cag aaa cag ctg ctg caa gag ctg caa gaa agc ttc ggt ggc cca acc<br>Gln Lys Gln Leu Leu Gln Glu Leu Gln Glu Ser Phe Gly Gly Pro Thr<br>360                         365                  370                  375 | | 1516 |
| ggc gag cac aac agc ccg cgc tca aag agc ttc ttt gat ggt gtg aag<br>Gly Glu His Asn Ser Pro Arg Ser Lys Ser Phe Phe Asp Gly Val Lys<br>                    380                  385                   390 | | 1564 |
| aag ttt ttt gac gac ctg acc cgc taa ggatccggct gagcaacgac<br>Lys Phe Phe Asp Asp Leu Thr Arg<br>             395                  400 | | 1611 |
| gtgaacgcaa tgcgttccga cgttcaggct gctaaagatg acgcagctcg tgctaaccag | | 1671 |
| cgtctggaca acatggctac taaataccgc aagtaatagt acctgtgaag tgaaaaatgg | | 1731 |
| cgcacattgt gcgacatttt ttttgtctgc cgtttaccgc tactgcgtca cgcgtaacat | | 1791 |
| attcccttgc tctggttcac cattctgcgc tgactctact gaaggcgcat tgctggctgc | | 1851 |
| gggagttgct ccactgctca ccgaaaccgg | | 1881 |

<210> SEQ ID NO 2
<211> LENGTH: 399
<212> TYPE: PRT
<213> ORGANISM: Escherichia coli

<400> SEQUENCE: 2

Met Lys Lys Thr Ala Ile Ala Ile Ala Val Ala Leu Ala Gly Phe Ala
1                 5                     10                     15

Thr Val Ala Gln Ala Gly Ile Pro Ala Lys Gln Asp Tyr Tyr Glu Ile
                   20                     25                   30

Leu Gly Val Ser Lys Thr Ala Glu Glu Arg Glu Ile Arg Lys Ala Tyr
               35                     40                   45

```
Lys Arg Leu Ala Met Lys Tyr His Pro Asp Arg Asn Gln Gly Asp Lys
            50                  55                  60

Glu Ala Glu Ala Lys Phe Lys Glu Ile Lys Glu Ala Tyr Glu Val Leu
 65                  70                  75                  80

Thr Asp Ser Gln Lys Arg Ala Ala Tyr Asp Gln Tyr Gly His Ala Ala
                 85                  90                  95

Phe Glu Gln Gly Gly Met Gly Gly Gly Phe Gly Gly Gly Ala Asp
                100                 105                 110

Phe Ser Asp Ile Phe Gly Asp Val Phe Gly Asp Ile Phe Gly Gly Gly
            115                 120                 125

Arg Gly Arg Gln Arg Ala Ala Arg Gly Ala Asp Leu Arg Tyr Asn Met
        130                 135                 140

Glu Leu Thr Leu Glu Glu Ala Val Arg Gly Val Thr Lys Glu Ile Arg
145                 150                 155                 160

Ile Pro Thr Leu Glu Glu Cys Asp Val Cys His Gly Ser Gly Ala Lys
                165                 170                 175

Pro Gly Thr Gln Pro Gln Thr Cys Pro Thr Cys His Gly Ser Gly Gln
            180                 185                 190

Val Gln Met Arg Gln Gly Phe Phe Ala Val Gln Gln Thr Cys Pro His
        195                 200                 205

Cys Gln Gly Arg Gly Thr Leu Ile Lys Asp Pro Cys Asn Lys Cys His
210                 215                 220

Gly His Gly Arg Val Glu Arg Ser Lys Thr Leu Ser Val Lys Ile Pro
225                 230                 235                 240

Ala Gly Val Asp Thr Gly Asp Arg Ile Arg Leu Ala Gly Glu Gly Glu
                245                 250                 255

Ala Gly Glu His Gly Ala Pro Ala Gly Asp Leu Tyr Val Gln Val Gln
            260                 265                 270

Val Lys Gln His Pro Ile Phe Glu Arg Glu Gly Asn Asn Leu Tyr Cys
        275                 280                 285

Glu Val Pro Ile Asn Phe Ala Met Ala Ala Leu Gly Gly Glu Ile Glu
290                 295                 300

Val Pro Thr Leu Asp Gly Arg Val Lys Leu Lys Val Pro Gly Glu Thr
305                 310                 315                 320

Gln Thr Gly Lys Leu Phe Arg Met Arg Gly Lys Gly Val Lys Ser Val
                325                 330                 335

Arg Gly Gly Ala Gln Gly Asp Leu Leu Cys Arg Val Val Val Glu Thr
            340                 345                 350

Pro Val Gly Leu Asn Glu Arg Gln Lys Gln Leu Leu Gln Glu Leu Gln
        355                 360                 365

Glu Ser Phe Gly Gly Pro Thr Gly Glu His Asn Ser Pro Arg Ser Lys
370                 375                 380

Ser Phe Phe Asp Gly Val Lys Lys Phe Phe Asp Asp Leu Thr Arg
385                 390                 395

<210> SEQ ID NO 3
<211> LENGTH: 1881
<212> TYPE: DNA
<213> ORGANISM: Escherichia coli
<220> FEATURE:
<221> NAME/KEY: CDS
<222> LOCATION: (392)..(790)

<400> SEQUENCE: 3
taggcgtatc acgaggccct ttggataacc agaagcaata aaaaatcaaa tcggatttca      60
```

-continued

```
ctatataatc tcactttatc taagatgaat ccgatggaag catcctgttt tctctcaatt      120
tttttatcta aaaccagcg ttcgatgctt ctttgagcga acgatcaaaa ataagtgcct       180
tcccatcaaa aaaatattct caacataaaa actttgtgt aatacttgta acgctacatg       240
gagattaact caatctagct agagaggctt tacactttat gcttccggct cgtataatgt     300
gtggaattgt gagcggataa caatttcaca caggaaacag ctatgaccat gattacggat     360
tcactggaac tctagataac gagggcaaaa a atg aaa aag aca gct atc gcg        412
                                   Met Lys Lys Thr Ala Ile Ala
                                    1               5 att gca gtg gca ctg gct ggt ttc gct acc gta gcg cag gcc gga att       460
Ile Ala Val Ala Leu Ala Gly Phe Ala Thr Val Ala Gln Ala Gly Ile
        10                  15                  20 cca gct aag caa gat tat tac gag att tta ggc gtt tcc aaa aca gcg       508
Pro Ala Lys Gln Asp Tyr Tyr Glu Ile Leu Gly Val Ser Lys Thr Ala
    25                  30                  35 gaa gag cgt gaa atc aga aag gcc tac aaa cgc ctg gcc atg aaa tac       556
Glu Glu Arg Glu Ile Arg Lys Ala Tyr Lys Arg Leu Ala Met Lys Tyr
40              45                  50                  55 cac ccg gac cgt aac cag ggt gac aaa gag gcc gag gcg aaa ttt aaa       604
His Pro Asp Arg Asn Gln Gly Asp Lys Glu Ala Glu Ala Lys Phe Lys
                60                  65                  70 gag atc aag gaa gct tat gaa gtt ctg acc gac tcg caa aaa cgt gcg       652
Glu Ile Lys Glu Ala Tyr Glu Val Leu Thr Asp Ser Gln Lys Arg Ala
            75                  80                  85 gca tac gat cag tat ggt cat gct gcg ttt gag caa ggt ggc atg ggc       700
Ala Tyr Asp Gln Tyr Gly His Ala Ala Phe Glu Gln Gly Gly Met Gly
        90                  95                  100 ggc ggc ggt ttt ggc ggc ggc gca gac ttc agc gat att ttt ggt gac       748
Gly Gly Gly Phe Gly Gly Gly Ala Asp Phe Ser Asp Ile Phe Gly Asp
    105                 110                 115 gtt ttc ggc gat att ttt ggc ggc gga cgt ggt cgt taa tag               790
Val Phe Gly Asp Ile Phe Gly Gly Gly Arg Gly Arg
120                 125                 130 gcggcgcgcg gtgctgattt acgctataac atggagctca ccctcgaaga agctgtacgt     850
ggcgtgacca aagagatccg cattccgact ctggaagagt gtgacgtttg ccacggtagc     910
ggtgcaaaac caggtacaca gccgcagact tgtccgacct gtcatggttc tggtcaggtg     970
cagatgcgcc agggattctt cgctgtacag cagacctgtc cacactgtca gggccgcggt   1030
acgctgatca agatccgtg caacaaatgt catggtcatg tcgtgttga gcgcagcaaa     1090 acgctgtccg ttaaaatccc ggcaggggtg gacactggag accgcatccg tcttgcgggc   1150
gaaggtgaag cgggcgagca tggcgcaccg gcaggcgatc tgtacgttca ggttcaggtt   1210
aaacagcacc cgattttcga gcgtgaaggc aacaacctgt attgcgaagt cccgatcaac   1270
ttcgctatgg cggcgctggg tggcgaaatc gaagtaccga cccttgatgg tcgcgtcaaa   1330
ctgaaagtgc ctggcgaaac ccagaccggt aagctattcc gtatgcgcgg taaaggcgtc   1390
aagtctgtcc gcgtggcgc acagggtgat ttgctgtgcc gcgttgtcgt cgaaacaccg   1450
gtaggcctga acgaaaggca gaaacagctg ctgcaagagc tgcaagaaag cttcggtggc   1510
ccaaccggcg agcacaacag cccgcgctca aagagcttct ttgatggtgt gaagaagttt   1570
tttgacgacc tgacccgcta aggatccggc tgagcaacga cgtgaacgca atgcgttccg   1630
acgttcaggc tgctaaagat gacgcagctc gtgctaacca gcgtctggac aacatggcta   1690
ctaaataccg caagtaatag tacctgtgaa gtgaaaaatg cgcacattg tgcgacattt    1750 tttttgtctg ccgtttaccg ctactgcgtc acgcgtaaca tattcccttg ctctggttca   1810
```

-continued

```
ccattctgcg ctgactctac tgaaggcgca ttgctggctg cgggagttgc tccactgctc      1870
accgaaaccg g                                                            1881
```

<210> SEQ ID NO 4
<211> LENGTH: 131
<212> TYPE: PRT
<213> ORGANISM: Escherichia coli

<400> SEQUENCE: 4

```
Met Lys Lys Thr Ala Ile Ala Ile Ala Val Ala Leu Ala Gly Phe Ala
  1               5                  10                  15

Thr Val Ala Gln Ala Gly Ile Pro Ala Lys Gln Asp Tyr Tyr Glu Ile
             20                  25                  30

Leu Gly Val Ser Lys Thr Ala Glu Glu Arg Glu Ile Arg Lys Ala Tyr
         35                  40                  45

Lys Arg Leu Ala Met Lys Tyr His Pro Asp Arg Asn Gln Gly Asp Lys
     50                  55                  60

Glu Ala Glu Ala Lys Phe Lys Glu Ile Lys Glu Ala Tyr Glu Val Leu
 65                  70                  75                  80

Thr Asp Ser Gln Lys Arg Ala Ala Tyr Asp Gln Tyr Gly His Ala Ala
                 85                  90                  95

Phe Glu Gln Gly Gly Met Gly Gly Gly Phe Gly Gly Ala Asp
                100                 105                 110

Phe Ser Asp Ile Phe Gly Asp Val Phe Gly Asp Ile Phe Gly Gly Gly
            115                 120                 125

Arg Gly Arg
        130
```

<210> SEQ ID NO 5
<211> LENGTH: 1379
<212> TYPE: DNA
<213> ORGANISM: Escherichia coli
<220> FEATURE:
<221> NAME/KEY: CDS
<222> LOCATION: (392)..(1090)

<400> SEQUENCE: 5

```
taggcgtatc acgaggccct ttggataacc agaagcaata aaaaatcaaa tcggatttca       60
ctatataatc tcactttatc taagatgaat ccgatggaag catcctgttt tctctcaatt      120
tttttatcta aacccagcg ttcgatgctt ctttgagcga acgatcaaaa ataagtgcct       180
tcccatcaaa aaatattct caacataaaa aactttgtgt aatacttgta acgctacatg      240
gagattaact caatctagct agagaggctt tacactttat gcttccggct cgtataatgt      300
gtggaattgt gagcggataa caatttcaca caggaaacag ctatgaccat gattacggat      360
tcactggaac tctagataac gagggcaaaa a atg aaa aag aca gct atc gcg          412
                                  Met Lys Lys Thr Ala Ile Ala
                                    1               5 att gca gtg gca ctg gct ggt ttc gct acc gta gcg cag gcc gga att          460
Ile Ala Val Ala Leu Ala Gly Phe Ala Thr Val Ala Gln Ala Gly Ile
           10                  15                  20 ctc acc gag cgc cgc gtg ccc ttc tcg ctg ctg cgg agc ccg agc tgg          508
Leu Thr Glu Arg Arg Val Pro Phe Ser Leu Leu Arg Ser Pro Ser Trp
     25                  30                  35 gaa cca ttc cgg gac tgg tac cct gca cac agc cgc ctc ttc gat caa          556
Glu Pro Phe Arg Asp Trp Tyr Pro Ala His Ser Arg Leu Phe Asp Gln
 40                  45                  50                  55
```

```
gct ttc ggg gtg ccc cgg ttg ccc gat gag tgg tcg cag tgg ttc agc    604
Ala Phe Gly Val Pro Arg Leu Pro Asp Glu Trp Ser Gln Trp Phe Ser
             60                  65                  70 gcc gct ggg tgg ccc gga tac gtg cgc ccg ctg ccc gcc gcg acc gcc    652
Ala Ala Gly Trp Pro Gly Tyr Val Arg Pro Leu Pro Ala Ala Thr Ala
             75                  80                  85 gag ggc ccc gcg gcg gtg acc ctg gcc gca cca gcc ttc agc cga gcg    700
Glu Gly Pro Ala Ala Val Thr Leu Ala Ala Pro Ala Phe Ser Arg Ala
         90                  95                 100 ctc aac cga cag ctc agc agc ggg gtc tcg gag atc cga cag acg gct    748
Leu Asn Arg Gln Leu Ser Ser Gly Val Ser Glu Ile Arg Gln Thr Ala
        105                 110                 115 gat cgc tgg cgc gtg tcc ctg gac gtc aac cac ttc gct ccg gag gag    796
Asp Arg Trp Arg Val Ser Leu Asp Val Asn His Phe Ala Pro Glu Glu
120                 125                 130                 135 ctc aca gtg aag acc aag gaa ggc gtg gtg gag atc act ggc aag cac    844
Leu Thr Val Lys Thr Lys Glu Gly Val Val Glu Ile Thr Gly Lys His
                140                 145                 150 gaa gaa agg cag gac gaa cat ggc tac atc tct cgg tgc ttc acc cgg    892
Glu Glu Arg Gln Asp Glu His Gly Tyr Ile Ser Arg Cys Phe Thr Arg
            155                 160                 165 aaa tac acg ctc cct cca ggt gtg gac ccc acc cta gtg tcc tct tcc    940
Lys Tyr Thr Leu Pro Pro Gly Val Asp Pro Thr Leu Val Ser Ser Ser
        170                 175                 180 cta tcc cct gag ggc aca ctt acc gtg gag gct ccg ttg ccc aaa gca    988
Leu Ser Pro Glu Gly Thr Leu Thr Val Glu Ala Pro Leu Pro Lys Ala
    185                 190                 195 gtc acg cag tca gcg gag atc acc att ccg gtt act ttc gag gcc cgc   1036
Val Thr Gln Ser Ala Glu Ile Thr Ile Pro Val Thr Phe Glu Ala Arg
200                 205                 210                 215 gcc caa att ggg ggc cca gaa gct ggg aag tct gaa cag tct gga gcc   1084
Ala Gln Ile Gly Gly Pro Glu Ala Gly Lys Ser Glu Gln Ser Gly Ala
                220                 225                 230 aag tag gatccggctg agcaacgacg tgaacgcaat gcgttccgac gttcaggctg   1140
Lys ctaaagatga cgcagctcgt gctaaccagc gtctggacaa catggctact aaataccgca   1200
agtaatagta cctgtgaagt gaaaaatggc gcacattgtg cgacatttt tttgtctgcc   1260 gtttaccgct actgcgtcac gcgtaacata ttcccttgct ctggttcacc attctgcgct   1320
gactctactg aaggcgcatt gctggctgcg ggagttgctc cactgctcac cgaaaccgg   1379
```

<210> SEQ ID NO 6
<211> LENGTH: 232
<212> TYPE: PRT
<213> ORGANISM: Escherichia coli

<400> SEQUENCE: 6

```
Met Lys Lys Thr Ala Ile Ala Ile Ala Val Ala Leu Ala Gly Phe Ala
  1               5                  10                  15

Thr Val Ala Gln Ala Gly Ile Leu Thr Glu Arg Arg Val Pro Phe Ser
             20                  25                  30

Leu Leu Arg Ser Pro Ser Trp Glu Pro Phe Arg Asp Trp Tyr Pro Ala
         35                  40                  45

His Ser Arg Leu Phe Asp Gln Ala Phe Gly Val Pro Arg Leu Pro Asp
     50                  55                  60

Glu Trp Ser Gln Trp Phe Ser Ala Ala Gly Trp Pro Gly Tyr Val Arg
 65                  70                  75                  80

Pro Leu Pro Ala Ala Thr Ala Glu Gly Pro Ala Ala Val Thr Leu Ala
```

```
                              85                      90                      95
        Ala Pro Ala Phe Ser Arg Ala Leu Asn Arg Gln Leu Ser Ser Gly Val
                        100                     105                     110

Ser Glu Ile Arg Gln Thr Ala Asp Arg Trp Arg Val Ser Leu Asp Val
                    115                     120                     125

Asn His Phe Ala Pro Glu Glu Leu Thr Val Lys Thr Lys Glu Gly Val
                130                     135                     140

Val Glu Ile Thr Gly Lys His Glu Glu Arg Gln Asp Glu His Gly Tyr
        145                     150                     155                     160

Ile Ser Arg Cys Phe Thr Arg Lys Tyr Thr Leu Pro Pro Gly Val Asp
                            165                     170                     175

Pro Thr Leu Val Ser Ser Leu Ser Pro Glu Gly Thr Leu Thr Val
                        180                     185                     190

Glu Ala Pro Leu Pro Lys Ala Val Thr Gln Ser Ala Glu Ile Thr Ile
                        195                     200                     205

Pro Val Thr Phe Glu Ala Arg Ala Gln Ile Gly Gly Pro Glu Ala Gly
                        210                     215                     220

Lys Ser Glu Gln Ser Gly Ala Lys
        225                     230

<210> SEQ ID NO 7
<211> LENGTH: 1256
<212> TYPE: DNA
<213> ORGANISM: Escherichia coli
<220> FEATURE:
<221> NAME/KEY: CDS
<222> LOCATION: (199)..(969)

<400> SEQUENCE: 7
gatctggctt tacactttat gcttccggct cgtatgttgt gtggaattgt gagcggataa      60
caatttcaca caggaaacag ctatgaccat gattacgcca agcttgcatg caaattctat     120
ttcaaggaga cagtcataat gaaataccta ttgcctacgg cagccgctgg attgttatta     180
ctcgcggccc agccggcc atg gcc gag gtc aag ctg cag gag tct ggg gga      231
                    Met Ala Glu Val Lys Leu Gln Glu Ser Gly Gly
                     1               5                      10 ggc tta gtg cag cct gga ggg tcc cgg aaa ctc tcc tgt gca gcc tct      279
Gly Leu Val Gln Pro Gly Gly Ser Arg Lys Leu Ser Cys Ala Ala Ser
            15                  20                  25 gga ttc act ttc agt agc ttt gga atg cac tgg gtt cgt cag gct cca      327
Gly Phe Thr Phe Ser Ser Phe Gly Met His Trp Val Arg Gln Ala Pro
        30                  35                  40 gag aag ggg ctg gag tgg gtc gca tat att agt agt ggc agt agt acc      375
Glu Lys Gly Leu Glu Trp Val Ala Tyr Ile Ser Ser Gly Ser Ser Thr
    45                  50                  55 atc tac tat gca gac aca gtg aag ggc cga ttc acc atc tcc aga gac      423
Ile Tyr Tyr Ala Asp Thr Val Lys Gly Arg Phe Thr Ile Ser Arg Asp
60                  65                  70                  75 aat ccc aag aac acc ctg ttc ctg caa atg acc agt cta agg tct gag      471
Asn Pro Lys Asn Thr Leu Phe Leu Gln Met Thr Ser Leu Arg Ser Glu
                80                  85                  90 gac acg gcc atg tat tac tgc gca aga gat tac ggg gct tat tgg ggc      519
Asp Thr Ala Met Tyr Tyr Cys Ala Arg Asp Tyr Gly Ala Tyr Trp Gly
            95                  100                 105 caa ggg acc acg gtc acc gtc tcc tca ggt gga ggc ggt tca ggc gga      567
Gln Gly Thr Thr Val Thr Val Ser Ser Gly Gly Gly Gly Ser Gly Gly
        110                 115                 120 ggt ggc tct ggc ggt ggc gga tcg gac att gag ctc acc cag tct cca      615
```

```
Gly Gly Ser Gly Gly Gly Ser Asp Ile Glu Leu Thr Gln Ser Pro
        125                 130                 135 gca atc atg tct gca tct cca ggg gag aag gtc acc atg acc tgc agt      663
Ala Ile Met Ser Ala Ser Pro Gly Glu Lys Val Thr Met Thr Cys Ser
140                 145                 150                 155 gcc agt tca agt gta agg tac atg aac tgg ttc caa cag aag tca ggc      711
Ala Ser Ser Ser Val Arg Tyr Met Asn Trp Phe Gln Gln Lys Ser Gly
                160                 165                 170 acc tcc ccc aaa aga tgg att tat gac aca tcc aaa ctg tct tct gga      759
Thr Ser Pro Lys Arg Trp Ile Tyr Asp Thr Ser Lys Leu Ser Ser Gly
            175                 180                 185 gtc cct gct cgc ttc agt ggc agt ggg tct ggg acc tct tac tct ctc      807
Val Pro Ala Arg Phe Ser Gly Ser Gly Ser Gly Thr Ser Tyr Ser Leu
        190                 195                 200 aca atc agc agc atg gag gct gaa gat gct gcc act tat tac tgc cag      855
Thr Ile Ser Ser Met Glu Ala Glu Asp Ala Ala Thr Tyr Tyr Cys Gln
    205                 210                 215 cag tgg agt agt aat cca ctc act ttc ggt gct ggg acc aag ctg gag      903
Gln Trp Ser Ser Asn Pro Leu Thr Phe Gly Ala Gly Thr Lys Leu Glu
220                 225                 230                 235 ctg aaa cgg gcg gcc gca gaa caa aaa ctc atc tca gaa gag gat ctg      951
Leu Lys Arg Ala Ala Ala Glu Gln Lys Leu Ile Ser Glu Glu Asp Leu
                240                 245                 250 aat ggg gcc gca tag taa ctgagcaacg acgtgaacgc aatgcgttcc              999
Asn Gly Ala Ala
            255 gacgttcagg ctgctaaaga tgacgcagct cgtgctaacc agcgtctgga caacatggct    1059 actaaatacc gcaagtaata gtacctgtga agtgaaaaat ggcgcacatt gtgcgacatt    1119 tttttttgtct gccgtttacc gctactgcgt cacgcgtaac atattcccctt gctctggttc  1179 accattctgc gctgactcta ctgaaggcgc attgctggct gcgggagttg ctccactgct    1239 caccgaaacc ggagatc                                                   1256

<210> SEQ ID NO 8
<211> LENGTH: 255
<212> TYPE: PRT
<213> ORGANISM: Escherichia coli

<400> SEQUENCE: 8

Met Ala Glu Val Lys Leu Gln Glu Ser Gly Gly Gly Leu Val Gln Pro
1               5                   10                  15

Gly Gly Ser Arg Lys Leu Ser Cys Ala Ala Ser Gly Phe Thr Phe Ser
            20                  25                  30

Ser Phe Gly Met His Trp Val Arg Gln Ala Pro Glu Lys Gly Leu Glu
        35                  40                  45

Trp Val Ala Tyr Ile Ser Ser Gly Ser Ser Thr Ile Tyr Tyr Ala Asp
    50                  55                  60

Thr Val Lys Gly Arg Phe Thr Ile Ser Arg Asp Asn Pro Lys Asn Thr
65                  70                  75                  80

Leu Phe Leu Gln Met Thr Ser Leu Arg Ser Glu Asp Thr Ala Met Tyr
                85                  90                  95

Tyr Cys Ala Arg Asp Tyr Gly Ala Tyr Trp Gly Gln Gly Thr Thr Val
            100                 105                 110

Thr Val Ser Ser Gly Gly Gly Ser Gly Gly Gly Ser Gly Gly
        115                 120                 125

Gly Gly Ser Asp Ile Glu Leu Thr Gln Ser Pro Ala Ile Met Ser Ala
    130                 135                 140
```

```
Ser Pro Gly Glu Lys Val Thr Met Thr Cys Ser Ala Ser Ser Ser Val
145                 150                 155                 160

Arg Tyr Met Asn Trp Phe Gln Gln Lys Ser Gly Thr Ser Pro Lys Arg
                165                 170                 175

Trp Ile Tyr Asp Thr Ser Lys Leu Ser Ser Gly Val Pro Ala Arg Phe
            180                 185                 190

Ser Gly Ser Gly Ser Gly Thr Ser Tyr Ser Leu Thr Ile Ser Ser Met
        195                 200                 205

Glu Ala Glu Asp Ala Ala Thr Tyr Tyr Cys Gln Gln Trp Ser Ser Asn
    210                 215                 220

Pro Leu Thr Phe Gly Ala Gly Thr Lys Leu Glu Leu Lys Arg Ala Ala
225                 230                 235                 240

Ala Glu Gln Lys Leu Ile Ser Glu Glu Asp Leu Asn Gly Ala Ala
                245                 250                 255

<210> SEQ ID NO 9
<211> LENGTH: 1137
<212> TYPE: DNA
<213> ORGANISM: Escherichia coli
<220> FEATURE:
<221> NAME/KEY: CDS
<222> LOCATION: (1)..(1137)

<400> SEQUENCE: 9 atg aaa tac ctg ctg ccg acc gct gct gct ggt ctg ctg ctc ctc gct      48
Met Lys Tyr Leu Leu Pro Thr Ala Ala Ala Gly Leu Leu Leu Leu Ala
 1               5                  10                  15 gcc cag ccg gcg atg gcc atg gct tac caa gga aac agt gac tgc tac      96
Ala Gln Pro Ala Met Ala Met Ala Tyr Gln Gly Asn Ser Asp Cys Tyr
                20                  25                  30 ttt ggg aat ggg tca gcc tac cgt ggc acg cac agc ctc acc gag tcg     144
Phe Gly Asn Gly Ser Ala Tyr Arg Gly Thr His Ser Leu Thr Glu Ser
            35                  40                  45 ggt gcc tcc tgc ctc ccg tgg aat tcc atg atc ctg ata ggc aag gtt     192
Gly Ala Ser Cys Leu Pro Trp Asn Ser Met Ile Leu Ile Gly Lys Val
        50                  55                  60 tac aca gca cag aac ccc agt gcc cag gca ctg ggc ctg ggc aaa cat     240
Tyr Thr Ala Gln Asn Pro Ser Ala Gln Ala Leu Gly Leu Gly Lys His
65                  70                  75                  80 aat tac tgc cgg aat cct gat ggg gat gcc aag ccc tgg tgc cac gtg     288
Asn Tyr Cys Arg Asn Pro Asp Gly Asp Ala Lys Pro Trp Cys His Val
                85                  90                  95 ctg acg aac cgc agg ctg acg tgg gag tac tgt gat gtg ccc tcc tgc     336
Leu Thr Asn Arg Arg Leu Thr Trp Glu Tyr Cys Asp Val Pro Ser Cys
            100                 105                 110 tcc acc tgc ggc ctg aga cag tac agc cag cct cag ttt cgc atc aaa     384
Ser Thr Cys Gly Leu Arg Gln Tyr Ser Gln Pro Gln Phe Arg Ile Lys
        115                 120                 125 gga ggg ctc ttc gcc gac atc gcc tcc cac ccc tgg cag gct gcc atc     432
Gly Gly Leu Phe Ala Asp Ile Ala Ser His Pro Trp Gln Ala Ala Ile
    130                 135                 140 ttt gcc aag cac agg agg tcg ccc gga gag cgg ttc ctg tgc ggg ggc     480
Phe Ala Lys His Arg Arg Ser Pro Gly Glu Arg Phe Leu Cys Gly Gly
145                 150                 155                 160 ata ctc atc agc tcc tgc tgg att ctc tct gcc gcc cac tgc ttc cag     528
Ile Leu Ile Ser Ser Cys Trp Ile Leu Ser Ala Ala His Cys Phe Gln
                165                 170                 175 gag agg ttt ccg ccc cac cac ctg acg gtg atc ttg ggc aga aca tac     576
Glu Arg Phe Pro Pro His His Leu Thr Val Ile Leu Gly Arg Thr Tyr
```

```
            180                 185                 190
cgg gtg gtc cct ggc gag gag gag cag aaa ttt gaa gtc gaa aaa tac      624
Arg Val Val Pro Gly Glu Glu Glu Gln Lys Phe Glu Val Glu Lys Tyr
            195                 200                 205 att gtc cat aag gaa ttc gat gat gac act tac gac aat gac att gcg      672
Ile Val His Lys Glu Phe Asp Asp Asp Thr Tyr Asp Asn Asp Ile Ala
    210                 215                 220 ctg ctg cag ctg aaa tcg gat tcg tcc cgc tgt gcc cag gag agc agc      720
Leu Leu Gln Leu Lys Ser Asp Ser Ser Arg Cys Ala Gln Glu Ser Ser
225                 230                 235                 240 gtg gtc cgc act gtg tgc ctt ccc ccg gcg gac ctg cag ctg ccg gac      768
Val Val Arg Thr Val Cys Leu Pro Pro Ala Asp Leu Gln Leu Pro Asp
                245                 250                 255 tgg acg gag tgt gag ctc tcc ggc tac ggc aag cat gag gcc ttg tct      816
Trp Thr Glu Cys Glu Leu Ser Gly Tyr Gly Lys His Glu Ala Leu Ser
            260                 265                 270 cct ttc tat tcg gag cgg ctg aag gag gct cat gtc aga ctg tac cca      864
Pro Phe Tyr Ser Glu Arg Leu Lys Glu Ala His Val Arg Leu Tyr Pro
        275                 280                 285 tcc agc cgc tgc aca tca caa cat tta ctt aac aga aca gtc acc gac      912
Ser Ser Arg Cys Thr Ser Gln His Leu Leu Asn Arg Thr Val Thr Asp
    290                 295                 300 aac atg ctg tgt gct gga gac act cgg agc ggc ggg ccc cag gca aac      960
Asn Met Leu Cys Ala Gly Asp Thr Arg Ser Gly Gly Pro Gln Ala Asn
305                 310                 315                 320 ttg cac gac gcc tgc cag ggc gat tcg gga ggc ccc ctg gtg tgt ctg     1008
Leu His Asp Ala Cys Gln Gly Asp Ser Gly Gly Pro Leu Val Cys Leu
                325                 330                 335 aac gat ggc cgc atg act ttg gtg ggc atc atc agc tgg ggc ctg ggc     1056
Asn Asp Gly Arg Met Thr Leu Val Gly Ile Ile Ser Trp Gly Leu Gly
            340                 345                 350 tgt gga cag aag gat gtc ccg ggt gtg tac acc aag gtt acc aac tac     1104
Cys Gly Gln Lys Asp Val Pro Gly Val Tyr Thr Lys Val Thr Asn Tyr
        355                 360                 365 cta gac tgg att cgt gac aac atg cga ccg tga                         1137
Leu Asp Trp Ile Arg Asp Asn Met Arg Pro
    370                 375

<210> SEQ ID NO 10
<211> LENGTH: 378
<212> TYPE: PRT
<213> ORGANISM: Escherichia coli

<400> SEQUENCE: 10

Met Lys Tyr Leu Leu Pro Thr Ala Ala Gly Leu Leu Leu Ala
 1               5                  10                  15

Ala Gln Pro Ala Met Ala Met Ala Tyr Gln Gly Asn Ser Asp Cys Tyr
                20                  25                  30

Phe Gly Asn Gly Ser Ala Tyr Arg Gly Thr His Ser Leu Thr Glu Ser
            35                  40                  45

Gly Ala Ser Cys Leu Pro Trp Asn Ser Met Ile Leu Ile Gly Lys Val
        50                  55                  60

Tyr Thr Ala Gln Asn Pro Ser Ala Gln Ala Leu Gly Leu Gly Lys His
65                  70                  75                  80

Asn Tyr Cys Arg Asn Pro Asp Gly Asp Ala Lys Pro Trp Cys His Val
                85                  90                  95

Leu Thr Asn Arg Arg Leu Thr Trp Glu Tyr Cys Asp Val Pro Ser Cys
            100                 105                 110
```

```
Ser Thr Cys Gly Leu Arg Gln Tyr Ser Gln Pro Gln Phe Arg Ile Lys
        115                 120                 125

Gly Gly Leu Phe Ala Asp Ile Ala Ser His Pro Trp Gln Ala Ala Ile
        130                 135                 140

Phe Ala Lys His Arg Arg Ser Pro Gly Glu Arg Phe Leu Cys Gly Gly
145                 150                 155                 160

Ile Leu Ile Ser Ser Cys Trp Ile Leu Ser Ala Ala His Cys Phe Gln
            165                 170                 175

Glu Arg Phe Pro Pro His His Leu Thr Val Ile Leu Gly Arg Thr Tyr
                180                 185                 190

Arg Val Val Pro Gly Glu Glu Glu Gln Lys Phe Glu Val Glu Lys Tyr
        195                 200                 205

Ile Val His Lys Glu Phe Asp Asp Thr Tyr Asp Asn Asp Ile Ala
        210                 215                 220

Leu Leu Gln Leu Lys Ser Asp Ser Ser Arg Cys Ala Gln Glu Ser Ser
225                 230                 235                 240

Val Val Arg Thr Val Cys Leu Pro Pro Ala Asp Leu Gln Leu Pro Asp
            245                 250                 255

Trp Thr Glu Cys Glu Leu Ser Gly Tyr Gly Lys His Glu Ala Leu Ser
            260                 265                 270

Pro Phe Tyr Ser Glu Arg Leu Lys Glu Ala His Val Arg Leu Tyr Pro
        275                 280                 285

Ser Ser Arg Cys Thr Ser Gln His Leu Leu Asn Arg Thr Val Thr Asp
        290                 295                 300

Asn Met Leu Cys Ala Gly Asp Thr Arg Ser Gly Gly Pro Gln Ala Asn
305                 310                 315                 320

Leu His Asp Ala Cys Gln Gly Asp Ser Gly Gly Pro Leu Val Cys Leu
                325                 330                 335

Asn Asp Gly Arg Met Thr Leu Val Gly Ile Ile Ser Trp Gly Leu Gly
                340                 345                 350

Cys Gly Gln Lys Asp Val Pro Gly Val Tyr Thr Lys Val Thr Asn Tyr
        355                 360                 365

Leu Asp Trp Ile Arg Asp Asn Met Arg Pro
370                 375
```

PROCESS FOR THE PRODUCTION OF NATURALLY FOLDED AND SECRETED PROTEINS BY CO-SECRETION OF MOLECULAR CHAPERONES

BACKGROUND OF THE INVENTION

1. Field

The invention concerns a process for the production of water-soluble, naturally folded and secreted polypeptides after expression in prokaryotic cells by co-secretion of molecular chaperones.

2. Description

Protein synthesis in prokaryotic organisms, which is also called translation, takes place on the ribosomes in the cytoplasm. When recombinant DNA is expressed in prokaryotic host organisms, it is often desirable to secrete the recombinant gene product or protein that is obtained in this process from the cytoplasm through the inner bacterial membrane into the periplasmic space between the inner and outer membrane. Secreted proteins can then be released from the periplasm into the nutrient medium for example by an osmotic shock. A disadvantage of this process is that the secreted polypeptides often do not form the native, biologically active conformation (Hockney, TIBTECH 12 (1994) 456–463).

Recently molecular chaperones and folding catalysts such as peptidyl-prolyl-cis/trans-isomerases or protein disulfide isomerases (Glockshuber et al., EP-A 0 510 658) have been used to increase the yield of native recombinant protein when folded in vivo (Thomas et al., Appl. Biochem. Biotechnol. 66 (1997) 197–238). In some cases this has led to considerable improvements in the expression e.g. of ribulose bisphosphate carboxylase (RUBISCO; Goloubinoff et al., Nature 337 (1989) 44–47), human procollagenase (Lee & Olins, J. Biol. Chem. 267 (1992) 2849–2852) or neuronal nitrogen oxide synthase from rats (Roman et al., Proc. Natl. Acad. Sci. USA 92 (1995) 8428–8432). In these examples GroEL/ES or the DnaK system from E. coli was co-overexpressed in the cytosol.

The co-expression of chaperones has also been examined when recombinant proteins are secreted into the periplasm of E. coli. However, in this case only a cytosolic overexpression of chaperones was evaluated in order to optimize secretion into the periplasm (Perez-Perez et al., Biochem. Biophys. Res. Commun. 210 (1995) 524–529; Sato et al., Biochem. Biophys. Res. Commun. 202 (1994) 258–264; Berges et al., Appl. Environ. Microbiol. 62 (1996) 55–60). Previous attempts at co-secretion in E. coli have concerned folding-helper proteins such as e.g. protein disulfide isomerase (PDI; Glockshuber et al., EP-A 0 510 658), peptidyl-prolyl-cis/trans-isomerases, Dsb proteins (Knappik et al., Bio/Technology 11 (1993) 77–83; Qiu et al., Appl. Environm. Microbiol. 64 (1998) 4891–4896 and Schmidt et al., Prot. Engin. 11 (1998) 601–607) or Skp protein (Hayhurst and Harris, Protein Expr. Purif 15 (1999) 336–343).

SUMMARY OF THE INVENTION

The subject invention provides a process for the production of a naturally folded eukaryotic polypeptide containing at least two cysteines linked by disulfide bridges. The process comprises culturing in a nutrient medium prokaryotic cells which contain (i) an expression vector that encodes the polypeptide, and contains a prokaryotic signal sequence at the N-terminus, and (ii) an expression vector that encodes a molecular chaperone. The culturing is under conditions such that the polypeptide and the chaperone is secreted into the periplasm of the prokaryotic cells or into the medium.

The signal sequence is cleaved from the polypeptide and the polypeptide is isolated. Preferably, the signal sequence is derived from gram-negative bacteria.

Preferably, a reducing thiol reagent, such as glutathione, can also be added to the nutrient medium. Preferably, the molecular chaperone is a small heat shock protein (sHsp type) or a heat shock protein with a molecular mass of about 40 kDa (Hsp40 type). The nucleic acid coding for the polypeptide and the chaperone can be located on one vector or on two separate vectors. The DNA encoding the molecular chaperone preferably is in operative linkage with DNA encoding a signal peptide for penetrating the inner bacterial membrane.

The DNA encoding the secreted protein is preferably under the control of an inducible expression signal. While not limiting the choice of polypeptide, the polypeptide can be an antibody, antibody fragment, interferon, protein hormone, or a protease.

DETAILED DESCRIPTION OF THE PREFERRED EMBODIMENT

Figure 1:
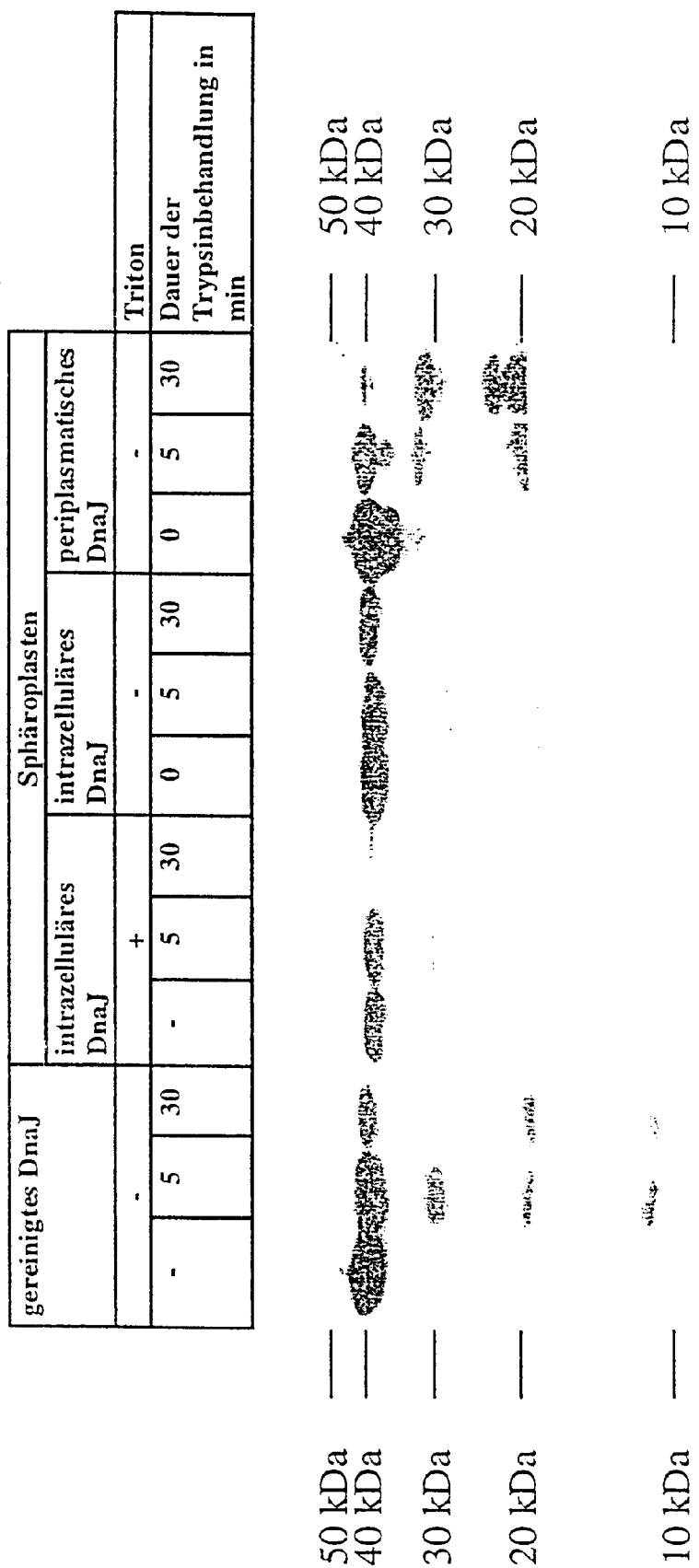
FIG. 1 shows a Western blot of the limited proteolysis of periplasmically and cytosolically expressed DnaJ with 50 μg/ml trypsin to detect the cellular location and native folding of the protein. The molecular weight standards were applied on the left and right. As a control, purified DnaJ (left) was subjected to the same procedure but using 6.25 μg/ml trypsin.
Figure 2:
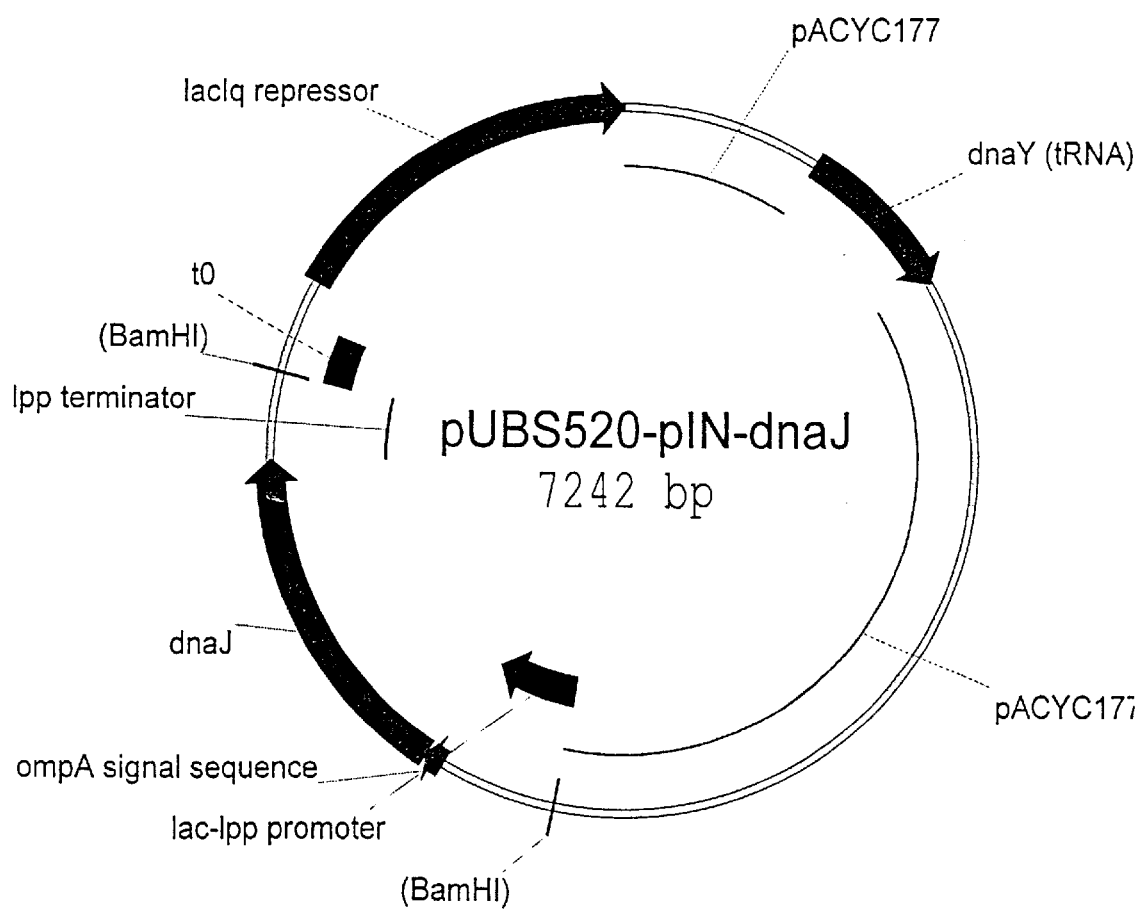
FIG. 2 shows a schematic representation of the expression plasmid pUBS520-pIN-dnaJ.
Figure 3:
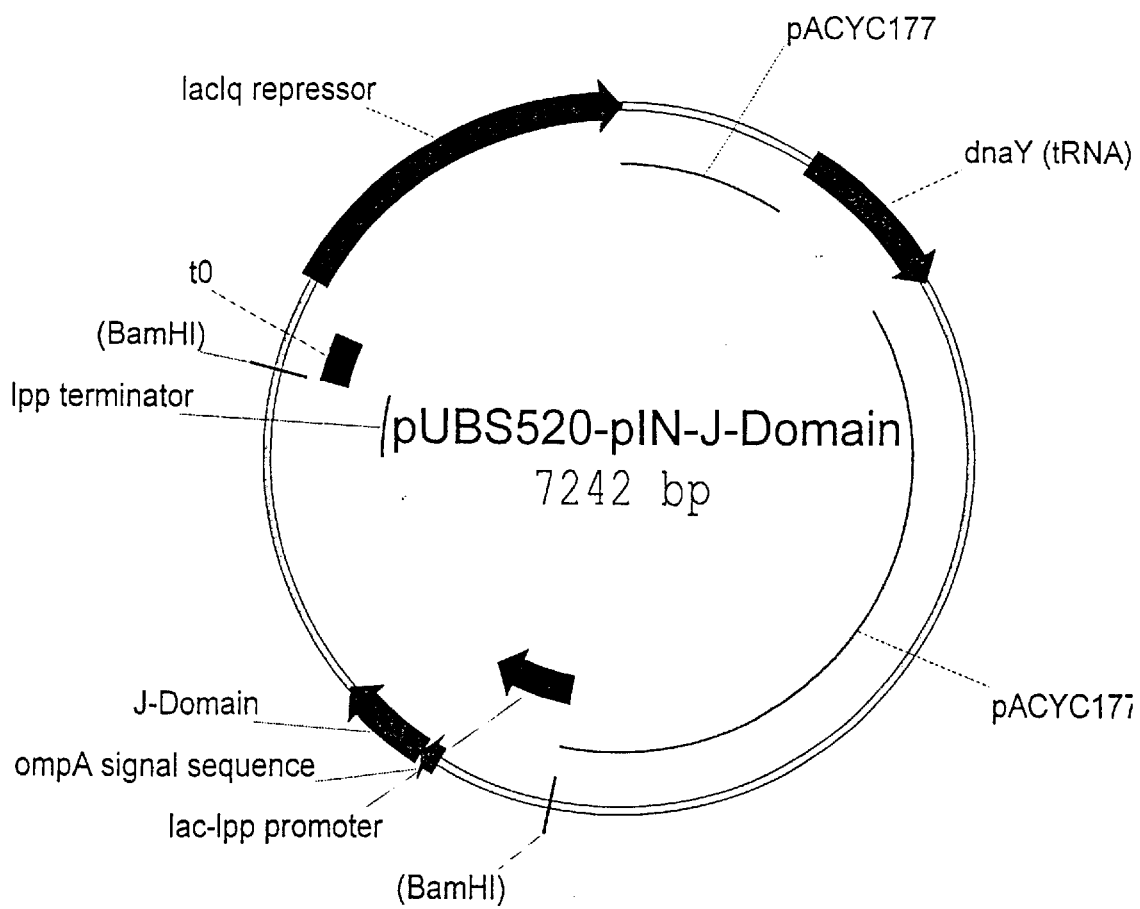
FIG. 3 shows a schematic representation of the expression plasmid pUBS520-pIN-J-Domain.

The subject invention provides a process for the production of water-soluble, naturally folded eukaryotic polypeptides after expression in prokaryotes which can be carried out in a simple manner preferably without a laborious in vitro after-treatment, such as dissolution, reduction and renaturation of inclusion bodies.

The object is achieved by a process for the production of a naturally folded eukaryotic polypeptide containing two or several cysteines linked by disulfide bridges by a) culturing prokaryotic cells in which the said prokaryotic cells contain an expression vector which codes for the said polypeptide which contains a prokaryotic signal sequence at the N-terminus, b) secreting the polypeptide into the periplasm or the medium, c) cleaving the signal sequence and isolating the polypeptide from the periplasm or the medium wherein a nucleic acid coding for a molecular chaperone is additionally expressed in the said prokaryotic cell and the chaperone is secreted into the periplasm. Preferably, the cultivation is performed without the presence of arginine or a compound of the general formula I $R_2$-CO-$NRR_1$ (I), in which R and $R_1$ represent independently hydrogen or a saturated or unsaturated branched or unbranched $C_1$–$C_4$ alkyl chain and $R_2$ represents hydrogen, NHR1 or a saturated or unsaturated branched or unbranched $C_1$–$C_3$ alkyl chain. In this process it is preferable that the chaperone is overexpressed.In a preferred embodiment of the process according to the invention, reducing thiol reagents which contain SH groups are additionally added to the nutrient medium (fermentation medium) used to culture the prokaryotic cells which further increases the yield of recombinantly produced protein. 0.1–15 mmol/l thiol reagent is preferably added. According to the invention the term "thiol reagent" either means a reducing (reduced) thiol reagent with SH groups or a mixture of reducing thiol reagents with SH groups and oxidizing thiol reagents with disulfide groups. Preferred substances are reduced glutathione (GSH), cysteine, N-acetylcysteine, cysteamine, β-mercaptoethanol and similar compounds. The thiol reagents can be used singly as well as in mixtures. Thiol reagents such as glutathione (GSH) which have a single SH group per molecule are particularly suitable. Thiol reagents such as glutathione are known to improve the yield of natively folded proteins when recombinant DNA is expressed in prokaryotic cells (Glockshuber et al., EP-A 0 510 658).

Chaperones are understood according to the invention as proteins which protect other non-native proteins from aggregation in vivo and promote the formation of their native conformation (Reviews: Silver and Way, Cell 74 (1994) 5–6 and Cyr et al., TIBS 19 (1994) 176–181). Molecular chaperones are used in the prior art to stabilize proteins and thus to protect them from aggregation and inactivation (Buchner et al., EP-A 0 556 726 A1). ATP-dependent chaperones of the HSP40 type (molar mass ca. 40 kDa) or a small heat shock protein (sHSP) are preferably used. DnaJ is a 40 kDa heat shock protein which occurs in the cytoplasm of E. coli and is a part of the so-called Hsp70 chaperone system (Bukau, B. & Horwich, A., Cell 92 (1998) 351–366). DnaK (Hsp70) and GrpE also belong to this system. Particular proteins are folded into the native conformation by the DnaK system in an ATP-dependent process (Schröder et al., EMBO J. 12 (1993) 4137–4144; Langer et al., Nature 356 (1992) 683–689). This system additionally requires ATP to refold denatured proteins. DnaJ protects non-native proteins from aggregation also in the absence of DnaK and ATP and mediates a folding-competent state (Schröder et al., EMBO J. 12 (1993) 4137–4144). The co-secretion of an N-terminal fragment of DnaJ which comprises the amino acids 1–108 and in the following is referred to as the J domain (Kelley, TIBS 23 (1998) 222–227) is additionally preferred. The J domain and a G/F-rich domain which are responsible for interactions with DnaK are located in this region (Wall et al., J. Biol. Chem. 270 (1995) 2139–2144). It has been shown that the co-expression of DnaJ in the cytosol can lead to an increase in the yield of soluble protein (Yokoyama et al., Microbiol. Ferment. Technol. 62 (1998) 1205–1210).

Hsp25 (e.g. from the mouse) is a representative of the small heat shock proteins (sHsps; Gaestel et al., Eur. J. Biochem. 179 (1989) 209–213) which are a ubiquitous class of chaperones. The molar mass of these proteins is between 15 and 30 kDa. During heat shock there is a substantial accumulation of sHsps in the cell (up to 1% of the total cell protein—Arrigo & Landry (1994), In Morimoto (Ed.): The Biology of Heat Shock Proteins and Molecular Chaperones, Cold Spring Harbour Press, 335–373). Like DnaJ proteins, sHsps have the property of preventing the aggregation of non-native proteins and of keeping these in a folding-competent state (Jakob et al., J. Biol. Chem. 268 (1993) 1517–1520; Ehrnsperger et al., EMBO J. 16 (1997) 221–229). All sHsps have regions which are homologous to the eukaryotic eye lens proteins αA and αB-crystallin which, in turn, are members of the sHsp family (Jakob and Buchner, TIBS 19 (1994) 205–211).

The term "overexpression" according to the present invention means an increase of the expression of secreted proteins such as e.g. DnaJ and Hsp25 (preferably by at least 100%) compared to expression in the wild-type of the respective prokaryotic host organism. Such an overexpression can for example be achieved when the genes (for the protein, chaperone and/or signal peptide) are under the control of a strong prokaryotic, preferably inducible, expression signal (e.g. of a lac or T7 promoter or a derivative thereof).

The secretion construct for the overexpression of polypeptides (proteins) including regulatory regions (promoter and terminator) on the recombinant DNA is preferably integrated into a vector which additionally codes the arginine-$tRNA_{AGA/AGG}$ which is rare in prokaryotes or it is co-expressed with a vector which codes for this tRNA (Brinkmann et al., Gene 85 (1989) 109–114). This enables the co-overexpression of the respective proteins into the bacterial periplasm as well as the transcription of the rare $tRNA^{Arg}_{AGA/AGG}$, which results in an increased synthesis of the desired protein in the bacterial host organism. The nucleic acid coding for the polypeptide and the chaperone can be located on one vector or on two separate vectors.

A prokaryotic signal sequence in the sense of the invention is understood as a nucleic acid fragment which is derived from prokaryotes, preferably from gram-negative bacteria, and ensures that proteins containing the signal peptide can penetrate through the inner bacterial membrane. As a result the proteins are located in the periplasm or in the cell supernatant. Such signal sequences usually have a length of 18–30 amino acids and are described for example in Murphy & Beckwith: Export of Proteins to the Cell Envelope in *Escherichia coli* and in Neidhardt et al. (editors): *Escherichia coli* and Salmonella, Second Edition, Vol. 1, ASM Press, Washington, 1996, p. 967–978. The cleavage of bacterial signal sequences can for example occur after an Ala-X-Ala sequence (von Heijne et al., J. Mol. Biol. 184 (1985) 99–105). The structure of the bacterial signal peptidase is described in Paetzel et al., Nature 396 (1998) 186–190. Signal sequences are preferably used that are cleaved again from the desired protein by proteases located in the periplasm of prokaryotic cells. Alternatively such proteases can be added to the cell supernatant or to the isolated protein to cleave the signal sequence.

The process according to the invention can improve the heterologous expression of numerous eukaryotic proteins such as e.g. proteases, interferons, protein hormones, antibodies or fragments thereof. The process is particularly suitable for the heterologous production of proteins which contain at least two cysteines linked by a disulfide bridge in their native state, especially when they have no prokaryotic signal sequence fused at the N-terminus and insoluble inclusion bodies are formed during their prokaryotic expression. The process is particularly suitable for proteins which contain more than 5 disulfide bridges in the native state. Such a protein is for example a recombinant plasminogen activator (referred to as rPA in the following, Martin et al., Cardiovasc. Drug Rev. 11 (1993) 299–311, U.S. Pat. No. 5,223,256). rPA has 9 disulfide bridges which are not formed in the reducing cytosol of E. coli.

The periplasmic location of the protein and of the chaperone is ensured by "operative linkage" with a signal peptide to penetrate the inner bacterial membranes.

In order to isolate the secretory rPA protein in a functional form in *E. coli*, the gene for this protein from the plasmid pA27fd7 (Kohnert et al., Protein Engineering 5 (1992) 93–100) was fused by genetic engineering methods to a prokaryotic signal sequence of gram-negative bacteria, for example to the signal sequence of pectate lyase B (PelB) from *Erwinia carotovora*. The gene fusion was constructed by cloning into the vector pET20b(+) (Novagen Inc., Madison, USA). As a result the gene expression is under the control of the T7 promoter. The signal sequence present in the fusion protein causes secretion into the periplasm. The signal sequence is cleaved during or after the secretion by a peptidase located in the inner membrane. The secreted protein can then fold in the periplasm. The oxidizing conditions in this compartment enable the formation of disulfide bridges (Wülfing und Plückthun, Mol. Microbiol. 12 (1994) 685–692). The simultaneous co-overexpression of DnaJ, J-domain or Hsp25 in the periplasm enables the yield of functional protein to be increased about 5- to 10-fold (Table 1).

The following examples, publications, the sequence listing and the figures further elucidate the invention, the protective scope of which results from the patent claims. The described methods are to be understood as examples which still describe the subject matter of the invention even after modifications.

Description of the Sequence Listing

SEQ ID NO: 1 shows the sequence of the part of the expression plasmid pUBS520-pIN-dnaj which codes for the fusion protein composed of the OmpA signal sequence and DnaJ together with the regulatory sequences (promoter, terminator) which was amplified from pIN III ompA3-dnaJ.

SEQ ID NO:2 shows the amino acid sequence of the OmpA-DnaJ fusion polypeptide.

SEQ ID NO: 3 shows the sequence of the part of the expression plasmid pUBS520-pIN-J-domain which codes for the fusion protein composed of the OmpA signal sequence and J domain together with the regulatory sequences (promoter, terminator) which was amplified from pIN III ompA3-dnaJ.

SEQ ID NO:4 shows the amino acid sequence of the OmpA-J-domain fusion polypeptide.

SEQ ID NO: 5 shows the sequence of the part of the expression plasmid pUBS520-pIN-hsp25 which codes for the fusion protein composed of the OmpA signal sequence and Hsp25 together with the regulatory sequences (promoter, terminator) which was amplified from pIN III ompA3-hsp25.

SEQ ID NO:6 shows the amino acid sequence of the OmpA-Hsp25 fusion polypeptide.

SEQ ID NO: 7 shows the sequence of the part of the expression plasmid pUBS520-ScFvOx which codes for the fusion protein composed of the PelB signal sequence and ScFvOxazolon together with the regulatory sequences (promoter, terminator) which was amplified from pHEN-ScFv or pIN III ompA3.

SEQ ID NO:8 shows the amino acid sequence of the PelB-scF$_v$oxazolon fusion polypeptide.

SEQ ID NO:9 shows the sequence of the part of the expression plasmid pET20b(+)-rPA which codes for the fusion protein composed of PelB signal sequence and rPA.

SEQ ID NO:10 shows the amino acid sequence of the PelB-rPA fusion polypeptide.

For the periplasmic overexpression of DnaJ, the J-domain and Hsp25 in *E. coli* , the DNA which codes for these proteins was fused by genetic engineering to the signal sequence of the outer membrane protein A (OmpA) of *E. coli* and the fusion was expressed in *E. coli* on a recombinant plasmid under the control of the lac-lpp promoter. As a result the polypeptide chain of DnaJ and Hsp25 are transported into the periplasm of the prokaryotic host organism and are natively folded there. Their location and native folding of DnaJ was demonstrated by limited proteolysis with trypsin and by Western blot.

EXAMPLE 1

Construction of the Expression Plasmid pIN III Omp A3-dnaJ

Molecular genetic techniques were based on Ausubel et al. (Ed.), J. Wiley & Sons, 1997, Curr. Protocols of Molecular Biology. Oligonucleotides were obtained from the companies MWG Biotech, Ebersberg or GIBCO Life Sciences, Eggenstein, GER.

The gene which codes for DnaJ, Gene Bank Accession No. M 12565, was cloned by means of the restriction cleavage sites EcoRI and BamHI into the expression plasmid pIN III ompA3 (Ghayreb et al., EMBO J. 3 (1984) 2437–2442). The sequence of the cloned PCR fragment was checked by dideoxy sequencing (LiCor DNA-Sequencer 4000, MWG Biotech, Ebersberg). The resulting plasmid was named pIN III ompA3-dnaJ. The sequence of the DnaJ expressed in the periplasm differs from that of the wild-type protein in that the polypeptide sequence begins with Gly-Ile-Pro instead of Met, hence there was an N-terminal extension of 2 amino acids. Hence DnaJ is under the control of the lac-lpp promoter which is induced with IPTG (isopropyl-β-D-thiogalactoside).

EXAMPLE 2

Construction of the Expression Plasmid pUBS520-pIN-dnaJ

The region from the plasmid pIN III ompA3-dnaJ which codes for the lac-lpp operon, the signal sequence, the dnaJ gene and the terminator region of the operon was amplified by means of PCR (SEQ ID NO: 1). The PCR product was cleaved with the restriction endonuclease BglII and cloned into the vector pUBS520 linearized with the restriction endonuclease BamHI. The resulting plasmid was named pUBS520-pIN-dnaJ (FIG. 2).

EXAMPLE 3

Construction of the Expression Plasmid pUBS 520-pIN-J-Domain

Two stop codons were inserted in the plasmid pUBS 520-pIN-dnaJ after the nucleotide 324 by means of the QuikChange mutagenesis system (Promega, Mannheim, Del.) so that only the first 108 amino acids are expressed. The sequence of the mutagenized region was determined by dideoxy sequencing (LiCor DNA-Sequencer 4000, MWG Biotech, Ebersberg) and the expression of the shortened protein fragment was detected by Western blotting and detection with an anti-DnaJ antibody. The plasmid that was formed was named pUBS 520-pIN-J-domain (FIG. 3).

EXAMPLE 4

Construction of the Expression Plasmid pIN III OmpA3-hsp25

The gene which codes for Hsp25, Gene Bank Accession No.: L 07577, was cloned by means of the restriction cleavage sites EcoRI and BamHI into the expression plasmid pIN III ompA3 (Ghayreb et al., EMBO J. 3 (1984) 2437–2442). The sequence of the cloned PCR fragment was checked by dideoxy sequencing (LiCor DNA-Sequencer 4000, MWG Biotech, Ebersberg). The resulting plasmid was named pIN III ompA3-hsp25. The sequence of the Hsp25 expressed in the periplasm differs from that of the wild-type protein in that the polypeptide sequence begins with Gly-Ile-Leu instead of Met, hence there was an N-terminal extension of 2 amino acids. Hence Hsp25 is under the control of the lac-lpp promoter which is induced with IPTG (isopropyl-β-D-thiogalactoside).

EXAMPLE 5

Construction of the Expression Plasmid pUBS520-pIN-hsp25

Figure 4:
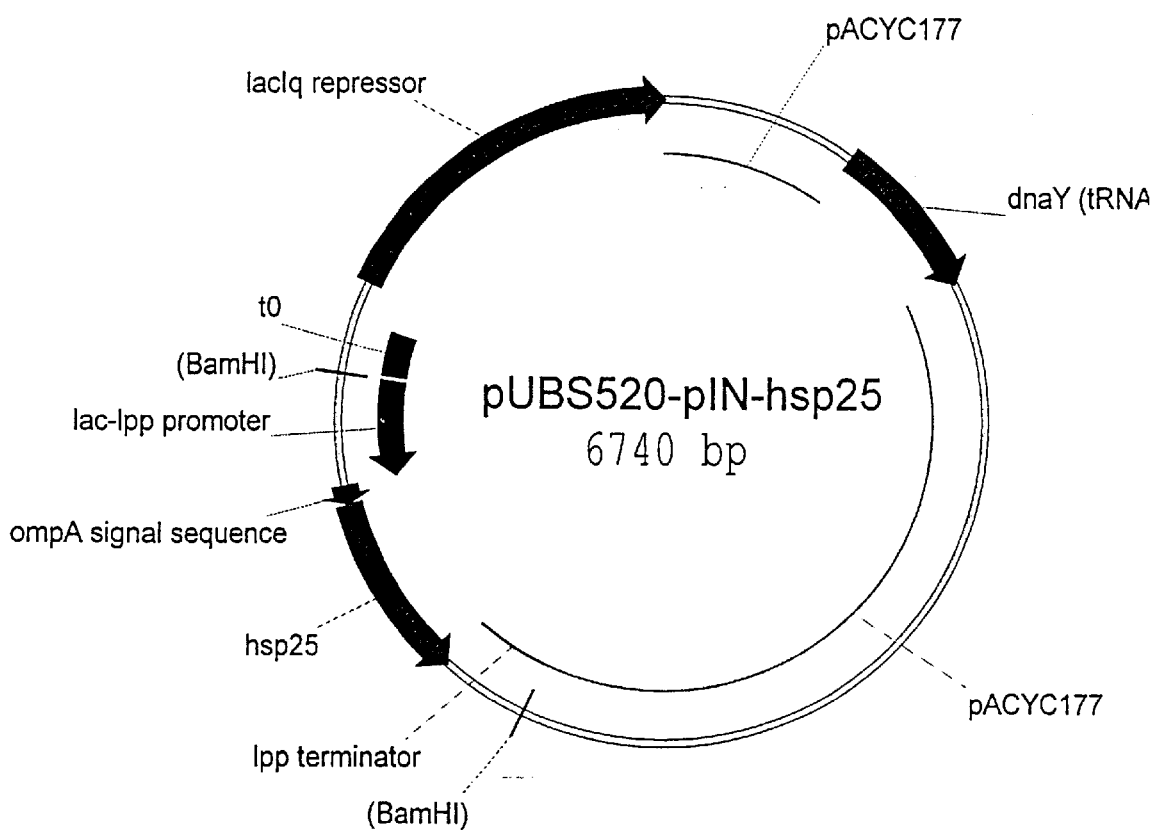
FIG. 4 shows a schematic representation of the expression plasmid pUBS520-pIN-hsp25.

The region from the plasmid pIN III ompA3-hsp25 which codes for the lac-lpp operon, the signal sequence, the hsp25 gene and the terminator region of the operon was amplified by means of PCR (SEQ ID NO: 5). The PCR product was cleaved with the restriction endonuclease BglII and cloned into the vector pUBS520 linearized with the restriction endonuclease BamHI. The resulting plasmid was named pUBS520-pIN-hsp25 (FIG. 4).

EXAMPLE 6

Construction of the Expression Plasmid pUBS520-ScFvOx

The co-expression of a single chain Fv fragment which is directed against the hapten oxazolon (ScFvOxazolon; Fiedler and Conrad, Bio/Technology 13 (1995) 1090–1093) which has no chaperone properties was examined as a negative control.

Figure 5:
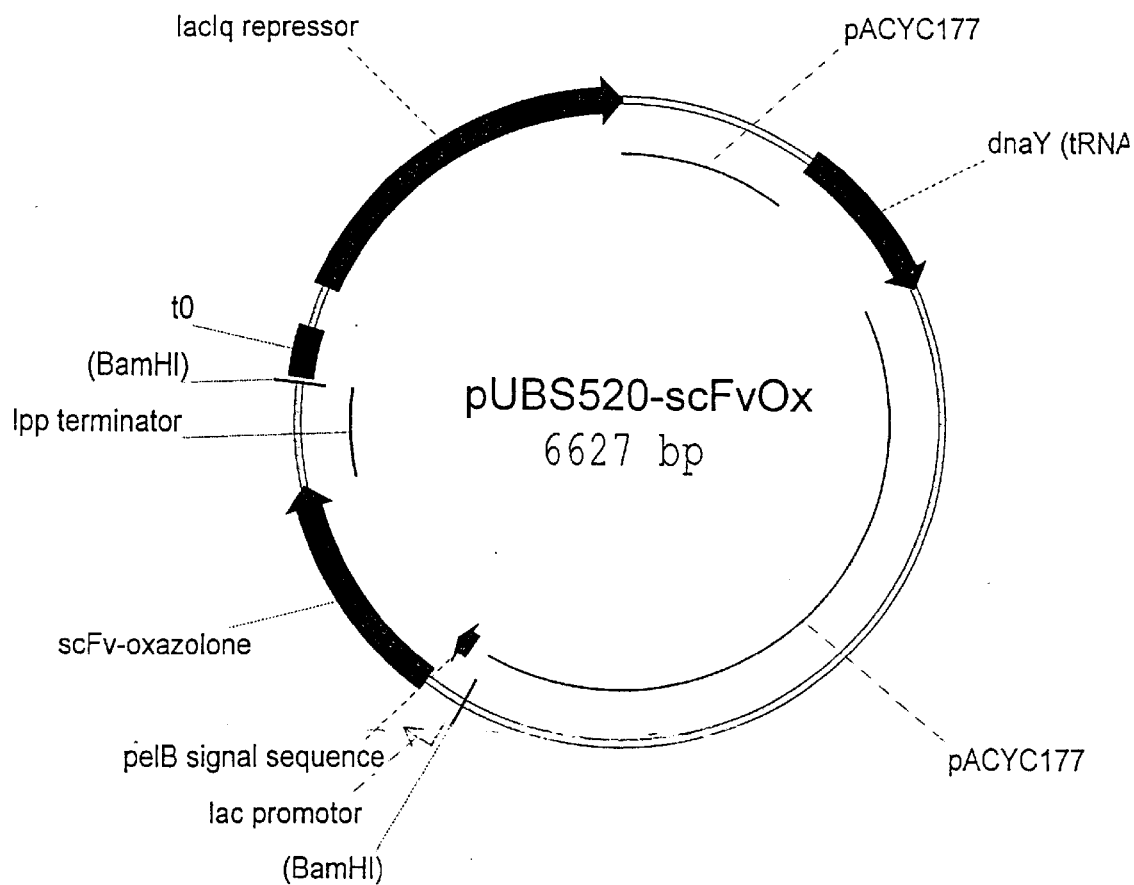
FIG. 5 shows a schematic representation of the expression plasmid pUBS520-ScFvOx.

The region from the plasmid pHEN-ScFvOx which codes for the lac promoter, the signal sequence pelB and the scfvox gene was amplified by means of PCR. The region from the plasmid pIN III ompA3 which codes for the lpp terminator was amplified in a second PCR. The two fragments were fused in a subsequent PCR. The PCR product (SEQ ID NO: 7) that was formed in this manner was cleaved with the restriction endonuclease BglII and cloned into the vector pUBS520 that was linearized with the restriction endonuclease BamHI. The resulting plasmid was named pUBS520-ScFvOx (FIG. 5).

EXAMPLE 7

Construction of the Expression Plasmid pET20b(+)-rPA

Figure 6:
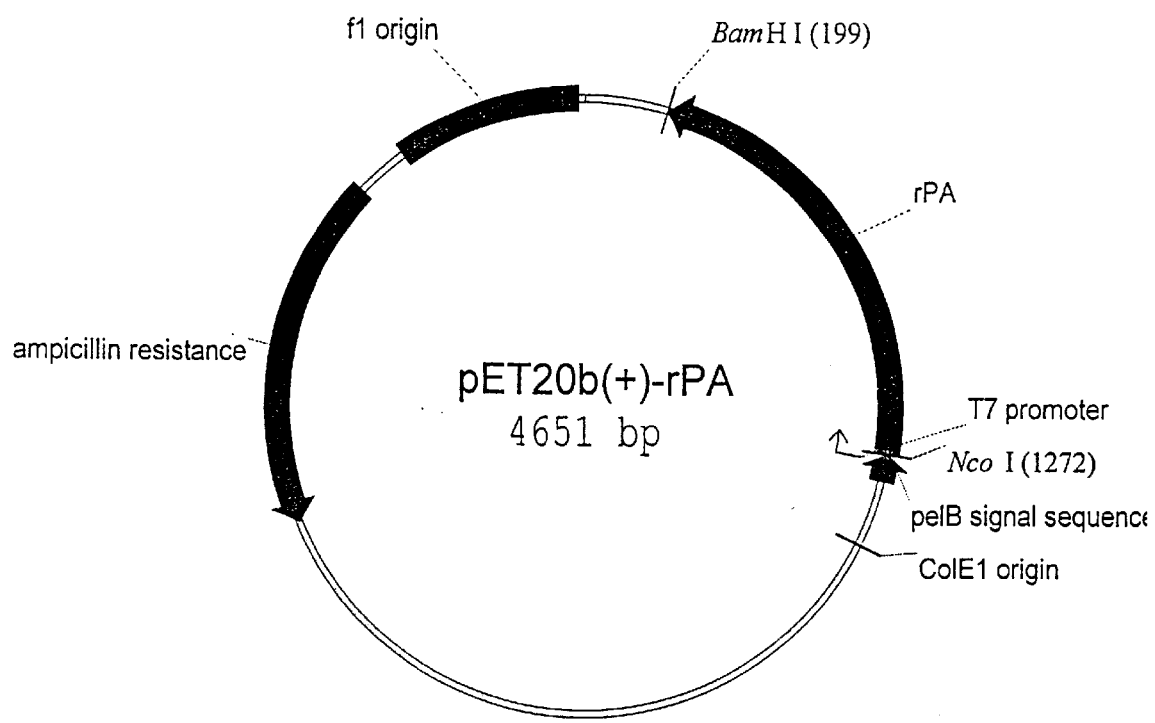
FIG. 6 shows a schematic representation of the expression plasmid pET20b(+)-rPA.

The gene of a plasminogen activator (rPA) from the plasmid vector pA27fd7 (Kohnert et al., Protein Engineering 5 (1992) 93–100) was amplified with the aid of a PCR method. The PCR product was cleaved with the restriction endonucleases NcoI and BamHI and cloned into the plasmid vector pET20b(+) (Novagen Inc., Madison, USA). The plasmid codes for a fusion protein which is composed of the signal sequence of PelB (pectate lyase from *Erwinia carotovora*) and rPA and the secretion of rPA into the periplasm was checked by dideoxy sequencing (LiCor DNA-Sequencer 4000, MWG Biotech, Ebersberg, Del.). The construct was named pET20b(+)-rPA (SEQ ID NO:10) (FIG. 6). rPA is expressed in the plasmid under the control of the T7 promoter, the T7-RNA-polymerase in the strain *E. coli* BL21(DE3) being under the control of the lacUV5 promoter. The induction was carried out by adding IPTG. The rPA expressed in the periplasm differs from the plasminogen activator described by Kohnert et al in that the second amino acid (Ser) is substituted by Ala.

EXAMPLE 8

Functional Expression of rPA in the Periplasm of *E. coli*

A stationary overnight culture of *E. coli* BL21(DE3) cells (Studier & Moffat, J. Mol. Biol. 189 (1986) 113–130) which contained pET20b(+)-rPA and pUBS520-pIN-dnaJ (co-expression of DnaJ), an overnight culture of *E. coli* BL21 (DE3) cells which contained pET20b(+)-rPA and pUBS520-pIN-J-domain (co-expression of the J-domain), an overnight culture of *E. coli* BL21(DE3) cells which contained pET20b (+)-rPA and pUBS520-pIN-hsp25 (co-expression of Hsp25), an overnight culture of *E. coli* BL21(DE3) cells which contained pET20b(+)-rPA and pUBS520-ScFvOx (co-expression of ScFvOx), an overnight culture of *E. coli* BL21(DE3) cells which contained pET20b(+)-rPA and pUBS520 or an overnight culture of *E. coli* BL21(DE3) cells which contained pET20b(+) and pUBS520 (control culture), was diluted in a ratio of 1:50 in 100 ml LB-Medium containing ampicillin (100 μg/ml) and kanamycin (50 μg/ml, Fluka Chemica, Neu-Ulm, GER) and shaken at 24° C. and 170 rpm. After 3 h growth, 5 ml aliquots of the culture were added to 10 ml LB medium containing the aforementioned amounts of ampicillin and kanamycin and 5 mM GSH (Fluka, GER) and each was induced with 1 mM IPTG (isopropyl-β-D-thiogalactoside, AppliChem, Darmstadt, GER). The cells were shaken for a further 21 h at 24° C. and 170 rpm and a 1 ml sample was taken after determining the $OD_{600}$. These 1 ml cell samples were fractionated in 2 ml Eppendorf reaction vessels by a modified protocol according to Jacobi et al. (J. Biol. Chem. 272 (1997) 21692–21699). In detail 500 μl fractionation buffer (150 mM NaCl (Roth GmbH), 50 mM Tris/HCl (Roth GmbH, 5 mM EDTA (Biomol) and 1 mg/ml polymyxin B sulfate (Sigma), pH 7.5) were added to the cell pellet, shaken for 1 h at 10° C. on an Eppendorf thermoshaker at 1400 rpm and then centrifuged for 15 min at 14 000 rpm in an Eppendorf microcentrifuge cooled to 10° C. to form a fraction containing the soluble periplasmic proteins (supernatant) and a residual fraction (pellet).

The activity of rPA was determined essentially according to the method of Verheijen et al. Thromb. Haemostasis 48 (1982) 266–269).

All determined rPA concentrations in the cell extracts were standardized to cell suspensions of $OD_{600}=1$ in order to correct the error that occurs when measuring in different buffers. The results are shown in Table 1.

TABLE 1

Effect of co-secretion of molecular chaperones on the formation of native rPA in the periplasm of E. coli in the presence of 5 mM GSH in the fermentation medium

| Co-secreted protein | RPA in ng/ml* $OD_{600}$ | Stimulation factor |
|---|---|---|
| — | 0.030 ± 0.001 | 29 |
| DnaJ | 0.197 ± 0.019 | 29 |
| J domain | 0.339 ± 0.007 | 16 |
| Hsp25 | 0.053 ± 0.002 | 27 |
| ScFvOxazolon (control) | 0.041 ± 0.003 | 13 |

EXAMPLE 9

Detection of the Periplasmic Location of DnaJ Which was Expressed By Means of pIN III OmpA3

Spheroplasts were prepared in order to prove the periplasmic location and correct folding of DnaJ which was secreted into the periplasm by means of pIN III ompA3-dnaJ. For this *E. coli* XLI blue cells containing pIN III ompA3-dnaJ were diluted 1:50 from a stationary preculture in LB medium (1 l LB medium contains 10 g Bacto-tryptone (Difco Factories, Detroit, Mich., USA), 5 g yeast (Difco Factories) and 5 g NaCl (Roth GmbH, Karlsruhe) containing 100 μg/ml ampicillin (Sigma, Deisenhofen), cultured at 37° C. and 200 rpm and induced after 2.75 h (OD$_{600}$ ca. 0.5) with 1 mM IPTG. After 3 h growth in the presence of the inducer, the cells were harvested by centrifugation (Eppendorf microcentrifuge, 5000 rpm, 5 min). An *E. coli* strain which contains a plasmid for the intracellular overexpression of DnaJ was cultured as a control and induced for 3 h. Spheroplasts were prepared as follows from the cell pellets obtained after centrifugation:

The equivalent of 2 ml bacteria which corresponds to an OD$_{600}$ of 1 were fractionated according to Thorstenson et al., J. Bacteriol. 179 (1997) 5333–5339. The spheroplasts which accumulate as a pellet were taken up in 30 μl 50 mM Tris/HCl, pH 8.0 containing 100 mM NaCl. As a control spheroplasts were taken up in the same buffer but with the addition of 0.1% Triton®-X-100 (Amresco, Solon, Ohio, USA). For a subsequent limited proteolysis with trypsin 15 μl of the respective spheroplast preparation (with or without Triton®-X-100) was mixed with 2 μl 1 mg/ml trypsin (Roche Diagnostics GmbH, GER) and 23 μl 50 mM Tris/HCl, pH 8.0 containing 100 mM NaCl and incubated at 20° C. After 0, 5 and 30 minutes 8 μl samples were taken, admixed with 2 μl 4 mg/ml soybean-trypsin inhibitor and 3 μl SDS-PAGE application buffer (4% glycerol (Sigma, Deisenhofen), 0.5% SDS (ICN), 2% mercaptoethanol (Sigma), 0.0625 M Tris/HCl, pH 6.8 and bromophenol blue (Sigma)) and boiled for 5 min. In a control experiment 2 μg purified DnaJ (2 μg/μl) were mixed with 1 μl 100 μg/ml trypsin and 14 μl 50 mM Tris/HCl, pH 8.0 containing 100 mM NaCl, incubated at 20° C. and the proteolysis was ended at the stated times. The proteolysis products were separated by SDS-PAGE according to Lämmli et al., Nature 227 (1970) 680–685). The separated proteins were transferred onto nitrocellulose membranes (RioRad Laboratories, Munich) (Khyse-Anderson, J. Biochem. Biophys. Methods 10 (1984) 203–207; Towbin et al., Proc. Natl. Acad. Sci. USA 79 (1979) 267–271). The membranes were blocked overnight with TBS-5% milk powder (Glücksklee, Nestlé Frankfurt) and subsequently decorated for 2 h with anti-DnaJ antibodies in TBS 5% milk powder. After 3 wash steps 5 min each time in TBS, they were incubated with an additional antibody (antirabbit-IgG peroxidase, Amersham Life Sciences, Braunschweig) in TBS-5% milk powder for 1.5 h and again washed 5× with TBS buffer. The ECL Western blotting detection kit from the Amersham Company was used for the detection. The result is shown in FIG. 1. Since the secreted chaperone is protease-sensitive after the spheroplast preparation this demonstrates that it is located on the periplasmic side of the inner membrane. In contrast intracellular DnaJ is still protease protected after spheroplast preparation. Permeabilization of the spheroplasts by Triton-X-100 leads to digestion of intracellular DnaJ by trypsin. The cleavage pattern of the DnaJ expressed in the periplasm is identical to that of purified native DnaJ. This therefore demonstrates that the periplasmic expression product is in a native form in this compartment.

LIST OF REFERENCES

Arrigo & Landry (1994) In Morimoto (publ.): The Biology of Heat Shock Proteins and Molecular Chaperones, Cold Spring Harbour Press, 335–373

Ausubel et al. (publ.) Current Protocols in Molecular Biology, J. Wiley & Sons, 1997

Berges et al., Appl. Environ. Microbiol. 62 (1996) 55–60

Brinkmann et al., Gene 85 (1989) 109–114

Bukau, B. & Horwich, A., Cell 92 (1998) 351–366

Cyr et al., TIBS 19 (1994) 176–181)

Ehrnsperger et al., EMBO J. 16 (1997) 221–229

EP-A 0 510 658

EP-A 0 556 726

Fiedler and Conrad, Bio/Technology 13 (1995) 1090–1093

Gaestel et al., Eur. J. Biochem. 179 (1989) 209–213

Ghayreb et al., EMBO J. 3 (1984) 2437–2442

Goloubinoffet al., Nature 337 (1989) 44–47

Hayhurst and Harris, Protein Expr. Purif. 15 (1999) 336–343

Hockney, TIBTECH 12 (1994) 456–463

Jacobi et al. (J. Biol. Chem. 272 (1997) 21692–21699

Jakob et al., J. Biol. Chem. 268 (1993) 1517–1520

Jakob and Buchner, TIBS 19 (1994) 205–211

Kelley, TIBS 23 (1998) 222–227

Khyse-Anderson, J. Biochem. Biophys. Methods 10 (1984) 203–207

Knappik et al., Bio/Technology 11 (1993) 77–83

Kohnert et al., Protein Engineering 5 (1992) 93–100

Lämmli et al., Nature 227 (1970) 680–685

Langer et al., Nature 356 (1992) 683–689

Lee & Olins, J. Biol. Chem. 267 (1992) 2849–2852

Martin et al., Cardiovasc. Drug Rev. 11 (1993) 299–311

Murphy & Beckwith: Export of Proteins to the Cell Envelope in *Escherichia coli*

Neidhardt et al. (publ.): *Escherichia coli* and Salmonella, Second Edition, Vol. 1, ASM Press, Washington, 1996, S. 967–978

Paetzel et al., Nature 396 (1998) 186–190

Perez-Perez et al., Biochem. Biophys. Res. Commun. 210 (1995) 524–529

Qiu et al., Appl. Environm. Microbiol. 64 (1998) 4891–4896

Roman et al., Proc. Natl. Acad. Sci. USA 92 (1995) 8428–8432

Sato et al., Biochem. Biophys. Res. Commun. 202 (1994) 258–264

Schmidt et al., Prot. Engin. 11 (1998) 601–607

Schröder et al., EMBO J. 12 (1993) 4137–4144

Silver and Way, Cell 74 (1994) 5–6

Studier & Moffat, J. Mol. Biol. 189 (1986) 113–130

Thomas et al., Appl. Biochem. Biotechnol. 66 (1997) 197–238

Thorstenson et al., J. Bacteriol. 179 (1997) 5333–5339

Towbin et al., Proc. Natl. Acad. Sci. USA 79 (1979) 267–271

U.S. Pat. No. 5,223,256

Verheijen et al. Thromb. Haemostasis 48 (1982) 266–269

Wall et al., J. Biol. Chem. 270 (1995) 2139–2144

Wülfing und Plückthun, Mol. Microbiol. 12 (1994) 685–692

Yokoyama et al., Microbiol. Ferment. Technol. 62 (1998) 1205–1210

What is claimed is:

1. A process for the production of a naturally-folded eukaryotic polypeptide containing at least two cysteines linked by disulfide bridges, which comprises
   a) culturing in a nutrient medium prokaryotic cells which contain (i) an expression vector that encodes the polypeptide, and contains a prokaryotic signal sequence at its N-terminus, and (ii) an expression vector that encodes a molecular chaperone naturally occurring in the cytoplasm of the prokaryotic cells, the culturing being under conditions such that the polypeptide and the chaperone is secreted into the periplasm of the prokaryotic cells or into the medium,
   b) cleaving the signal sequence from the polypeptide; and
   c) isolating the polypeptide.

2. The process as claimed in claim 1, wherein the chaperone is a small heat shock protein (sHsp type) or a heat shock protein with a molar mass of about 40 kDa (Hsp40 type).

3. The process as claimed in claim 2, wherein a reducing thiol reagent is added to the nutrient medium.

4. The process as claimed in claim 3, wherein glutathione (GSH) is the reducing thiol reagent.

5. The process as claimed in claim 4, wherein the signal sequence is derived from gram-negative bacteria.

6. The process as claimed in claim 5, wherein the vector encoding the molecular chaperone and the vector encoding the polypeptide are two separate vectors.

7. The process as claimed in claim 5, wherein the vector encoding the molecular chaperone and the vector encoding the polypeptide are the same vector.

8. The process as claimed in claim 6, wherein vector encoding the molecular chaperone contains recombinant DNA encoding the molecular chaperone in operative linkage with DNA encoding a signal peptide for penetrating the inner bacterial membrane.

9. The process as claimed in claim 7, wherein vector contains recombinant DNA encoding the molecular chaperone in operative linkage with DNA encoding a signal peptide for penetrating the inner bacterial membrane.

10. The process as claimed in claim 8, wherein the DNA encoding the secreted molecular chaperone and/or for the secreted protein is under the control of an inducible expression signal.

11. The process as claimed in claim 8, wherein the DNA encoding the secreted molecular chaperone is under the control of an inducible expression signal.

12. The process as claimed in claim 8, wherein the DNA encoding the secreted protein is under the control of an inducible expression signal.

13. The process as claimed in claim 9, wherein the DNA encoding the secreted molecular chaperone is under the control of an inducible expression signal.

14. The process as claimed in claim 9, wherein the DNA encoding the secreted protein is under the control of an inducible expression signal.

15. The process as claimed in claim 8, wherein the polypeptide is an antibody, antibody fragment, interferon, protein hormone or a protease.

16. The process as claimed in claim 8, wherein the polypeptide is an antibody, antibody fragment, interferon, protein hormone or a protease.

* * * * *